United States Patent

Andrews

[11] Patent Number: 5,609,568
[45] Date of Patent: Mar. 11, 1997

[54] ANTERIOR FLOOR-REACTION TYPE ANKLE-FOOT ORTHOSIS

[75] Inventor: Brian Andrews, Riverbend, Canada

[73] Assignee: University of Alberta, Edmonton, Canada

[21] Appl. No.: 360,680

[22] PCT Filed: Jun. 29, 1993

[86] PCT No.: PCT/GB93/01354

§ 371 Date: Mar. 13, 1995

§ 102(e) Date: Mar. 13, 1995

[87] PCT Pub. No.: WO94/00083

PCT Pub. Date: Jan. 6, 1994

[30] Foreign Application Priority Data

Jun. 30, 1992 [GB] United Kingdom .................. 9113876

[51] Int. Cl.⁶ ............................................. A61F 5/00
[52] U.S. Cl. ............................................. 602/28; 602/23
[58] Field of Search ............................ 602/23, 27, 28, 602/29

[56] References Cited

U.S. PATENT DOCUMENTS 4,497,070  2/1985  Cho ..................................... 602/27 X
5,219,324  6/1993  Hall .................................... 602/27 X

FOREIGN PATENT DOCUMENTS

3537360A1  2/1987  European Pat. Off. .
0372452  12/1988  European Pat. Off. .

Primary Examiner—Linda C. Dvorak
Attorney, Agent, or Firm—Nikaido, Marmelstein, Murray & Oram LLP

[57] ABSTRACT

An interior moulded floor-reaction (FR) ankle-foot (AFO) (10) is described which has a fixed ankle angle and a detachable heel wedge (16) which allows the vertical alignment of the brace to be adjusted. The anterior leg portion (12a) has an elastic calf strap (14) for controlling plantar flexion. The AFO is moulded in a single piece of plastic with the leg portion (12a) being integral with the foot portion (12b) and the elastic strap (14) passes around the back of the calf. The FR AFO fits inside the patient's shoe.

10 Claims, 1 Drawing Sheet

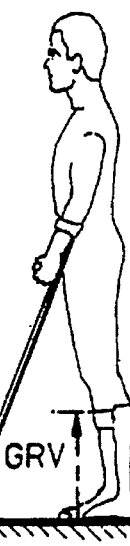
FIG.1a  FIG.1b
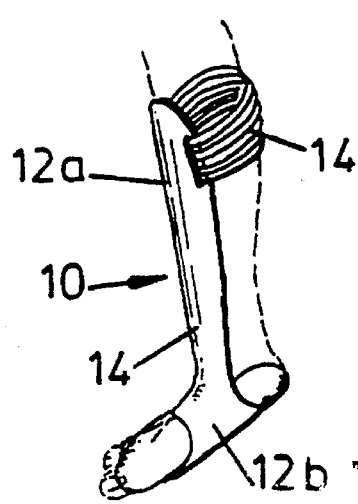
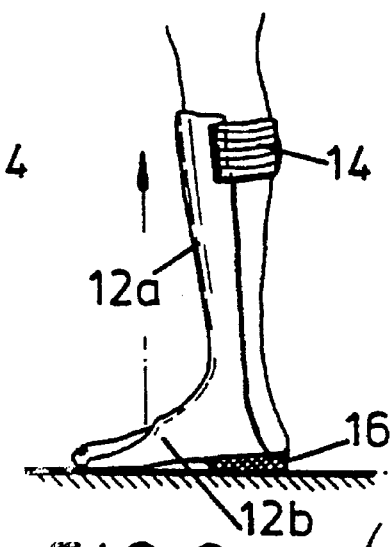
FIG.2  FIG.3
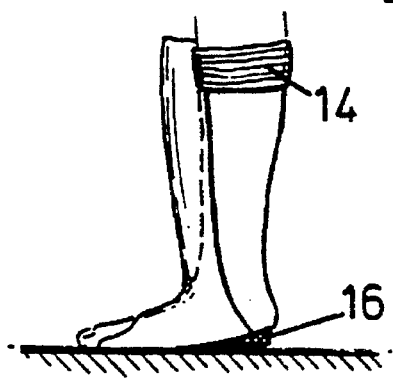
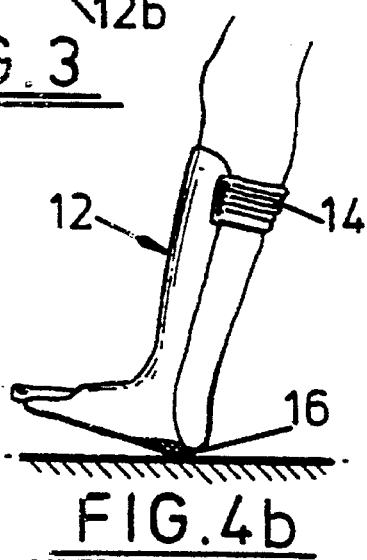
FIG.4a  FIG.4b

ANTERIOR FLOOR-REACTION TYPE
ANKLE-FOOT ORTHOSIS

TITLE OF THE INVENTION

The present invention relates to floor-reaction type ankle-foot orthosis.

BACKGROUND OF THE INVENTION

An anterior floor-reaction orthosis (AFRO) is a brace that prevents the ankle joint from dorsiflexing. In the case of a paralysed limb, without any brace, the ground reaction vector passes through the ankle joint because no torque can be transmitted. However, with an AFRO, the base of the ground reaction vector can be moved forward to the metatarsal region of the foot as shown in FIG. 1a. In this position the ground reaction vector acts ahead of the anatomical knee joint axis and thus stabilises the knee in extension without muscular action.

Traditionally, a paralysed leg is braced using a knee-ankle-foot orthosis (KAFO) that incorporates a mechanically lockable joint positioned at the side of the anatomical knee. In contrast, the anterior floor-reaction orthosis (AFRO) principle may be used to stabilise the paralysed leg without physically locking the knee in extension. This has the major advantage that during the swing phase of walking the knee can flex to gain ground clearance. In addition, this provides improved cosmesis and reduces weight and cumbrance. However, the AFRO only stabilises the knee on the condition that the ground reaction vector is ahead of the knee axis as shown in FIG. 1a. If the ground reaction vector should shift behind the knee as shown in FIG. 1b, then the knee would buckle and the leg would collapse if there were no knee extensor muscle action. Thus, the AFRO is only used or prescribed when the patient has sufficient control of his knee extensor musculature to avoid collapse in these situations. Alternatively, paralysed muscles may be electrically activated in response to such an incident as disclosed in U.S. Pat. No. 5,121,747.

SUMMARY OF THE INVENTION

An object of the present invention is to provide an improved floor-reaction orthosis which obviates or mitigates at least one of the aforementioned disadvantages.

This is achieved by providing a moulded plastic orthosis shell formed to be in close approximation to the anatomical limb. The leg portion of the plastic shell includes an elastic calf strap for controlling plantarflexion and a detachable heel wedge is provided which allows the vertical alignment of the brace to be adjusted. The improved foot-ankle orthosis fits inside the patient's shoe.

In one arrangement the floor-reaction orthosis is moulded in a single piece of plastic with the leg portion being integral with foot portion and the elastic strap is fastened to the top of the leg portion and passes round the back of the calf. The brace is fabricated such that the foot portion is made in one angled position which is typically 10° plantarflexion. This allows various heel wedges to be inserted beneath the heel to allow correct vertical alignment of the subject in the brace so that the correct ground reaction vector position is achieved. This permits accommodation of variations presented by different shoe heel heights.

The device is straightforward to fabricate and uses a thermoformed plastic sheet or fibre composite laminate which is made by thermoforming the plastic sheet over a plaster of paris mould of the patient's leg.

According to one aspect of the present invention, there is provided a floor-reaction orthosis comprising a below-knee moulded orthosis shell proportioned and dimensioned to be in close proximity to the anatomical limbs, said shell having a leg portion and a foot portion, said leg portion fitting over the anterior surface of the limb, and the foot portion being coupled to the leg portion to wrap around the foot, said leg portion having an elastic strap coupled thereto for fitting around the calf of the limb, said shell being moulded for a single ankle position of plantarflexion, said foot portion being adapted to receive separate heel means for providing, in use, correct vertical alignment of the subject in the orthosis whereby the correct ground reaction vector position is achieved.

The leg and foot portion are integrally moulded and fabrication is achieved by thermoforming a plastic sheet over a plaster of paris cast of the patient's leg. The orthosis may be moulded in a specific angle of plantarflexion depending on the requirements of a particular patient and the elastic strap can be fixed to the anterior surface of the orthosis by a number of ways, for example, slots may be moulded in the anterior surface and the strap passed therethrough or else the strap may be secured to the orthosis by fastening means, such as rivets and the like.

According to another aspect of the present invention there is provided a floor-reaction orthosis comprising a moulded anterior limb portion integral with a foot portion, the limb portion having an elastic strap coupled thereto for fitting around the calf of the limb, and the moulded portion being mould to a specific angle of plantarflexion for accommodating heel wedges to provide correct vertical alignment of the subject in the orthosis.

These and other aspects of the present invention will become apparent from the following description when taken in combination with the accompanying drawings in which:

BRIEF DESCRIPTION OF THE DRAWINGS

FIGS. 1a and 1b are views showing the ground reaction vector;

FIG. 2 is a perspective view of an embodiment of a floor-reaction orthosis (FRO) in accordance with the present invention;

FIG. 3 is a side view of a limb fitted with the floor-reaction orthosis shown in FIG. 2 with an adjustable heel wedge;

FIGS. 4a and 4b depict how the control of plantarflexion is achieved with the FRO by means of the elastic strap.

DESCRIPTION OF THE PREFERRED EMBODIMENT

Reference is first made to FIG. 2 of the drawings which depicts a floor-reaction orthosis generally indicated by reference numeral 10 which consists of a plastic moulded shell 12 which is formed to fit the front of the calf and the foot of the patient and which has an elastic strap 14 attached thereto for securing the anterior shell portion 12a to the patient's leg. The plastic shell is fabricated from thermoformed plastic sheet or fibre composite laminates by thermoforming the sheet over a plaster of paris mould of the patient's leg. As best seen in FIG. 3, the orthosis shell 12 is fabricated in a single angle position such that when fitted to-the-subject as shown in FIG. 3, there is a space between the heel of the subject and the floor. This allows a plastic heel wedge 16 to be inserted at the heel to allow the correct vertical alignment of the subject in the brace so that the correct ground reaction vector (GRV) position is achieved; this means that the GRV passes in front of the knee as shown in FIG. 3. The angle of fabrication is typically 10° of plantarflexion and can accommodate variations presented by different shoe heel heights.

Reference is now made to FIGS. 4a and 4b of the drawings which depicts the control of plantarflexion by means of the elastic strap 14. The elastic strap 14 stretches to provide plantarflexing control during the foot contact to foot-flat phase of early stance phase as indicated in FIGS. 4a and 4b respectively. The traditional ankle-foot orthosis immobilises plantarflexion and produces an unnatural gait similar to walking in rigid boots, for example, ski boots. With the present floor-reaction orthosis natural gait is facilitated because a natural rollover is provided similar to normal walking. At heel contact as shown in FIG. 4a, the heel portion 16 contacts the ground first and as forward movement occurs the orthosis leads the leg by virtue of the elastic strap 14 mimicing natural rollover and as the forward motion of the subject continues, the orthosis is retained on the leg as shown in FIG. 3.

The embodiment hereinbefore described provides a number of advantages over the prior art devices. Because the orthosis is moulded in a single piece, ankle joint components are not required and it is straightforward to fabricate the shell using thermoformed plastic sheet or fibre composite laminates. In addition, with the new floor-reaction orthosis for a given thickness of plastic material, the new shell is stiffer in resisting dorsiflexion. This allows thinner section materials to be used which in turn allows a shoe size closer to, or the same as, the patient's to be used. In a traditional ankle-foot orthosis it is usually necessary to go up at least one shoe size to accommodate the orthosis thereby adding unnecessary weight and foot length that adversely affects ground clearance during swing phase. With present orthosis no extra foot length is required facilitating natural rollover and providing cosmesis which is also important.

The elastic strap provides plantarflexion control during the foot contact to foot-flat phase of early stance phase as hereinbefore described whereas the traditional ankle-foot orthosis immobilises plantarflexion and produces an unnatural gait similar to walking in rigid boots. The plastic heel wedge allows the correct vertical alignment of the subject in the brace so that the correct ground reaction vector position is achieved. This allows the brace to be fabricated with one ankle position which is typically 10° plantarflexion, but accommodates variations presented by the different shoe heel heights.

It will also be understood that the floor-reaction orthosis hereinbefore described could be used in combination with a functional electrical stimulation system, such as disclosed in U.S. Pat. No. 5,121,747 or could be used by itself.

I claim:

1. A floor-reaction orthosis comprising a below-knee moulded anterior floor-reaction orthosis shell proportioned and dimensioned to be in close proximity to the anatomical limbs, said shell having a rigid leg portion and a foot portion, said leg portion fitting over the anterior surface of the limb and adapted to permit the limb to pull away from being in contact with the leg portion when in a standing state, and the foot portion being coupled to the leg portion adapted to wrap around the foot, said leg portion having an elastic strap coupled thereto adapted to fit around the calf of the limb, said shell being moulded for a single ankle position of plantarflexion; and a separate heel means on said foot portion for providing correct vertical alignment of the subject in orthosis whereby a predetermined ground reaction vector position is achieved.

2. A floor-reaction orthosis as claimed in claim 1 wherein the orthosis is moulded in a specific angle of plantarflexion.

3. A floor-reaction orthosis as claimed in claim 2 wherein the specific angle is about 10° plantarflexion.

4. A floor-reaction orthosis as claimed in claim 1 wherein said separate heel means is a wedge-shaped element.

5. A floor-reaction orthosis as claimed in any preceding claim further comprising slots are located in an anterior surface of the orthosis and wherein said elastic strap passes through the slots.

6. A floor-reaction orthosis as claimed in claim 1 wherein the elastic strap is secured to an anterior surface of the orthosis by rivets.

7. A floor-reaction orthosis comprising an anterior floor reaction orthosis with a moulded anterior limb portion integral with a foot portion wherein the limb portion is adapted to permit a limb to pull away in a controlled manner from being in contact with the limb portion in a standing state, the limb portion having an elastic strap coupled thereto for fitting around the calf of the limb, and the moulded portion being moulded to a specific angle of plantarflexion for accommodating heel wedges to provide correct vertical alignment of the subject in the orthosis; and a heel wedge attached to said foot portion.

8. An orthosis comprising:

an anterior floor-reaction orthosis shell with a foot portion and an anterior limb surface portion;

a posterior limb surface support means for holding a limb against an inside surface of said anterior limb portion during a limb swing state and for permitting said limb to pull away in a controlled manner from said interior surface of said anterior limb portion during a stance state and a vertical alignment device attached to a bottom heel portion of said foot portion.

9. An orthosis as claimed in claim 8 wherein said posterior limb surface support means comprises an elastic band.

10. An orthosis as claimed in claim 8 wherein said vertical alignment device comprises a wedge-shaped heel.

\* \* \* \* \*